United States Patent
Hellmuth et al.

(10) Patent No.: US 10,975,335 B2
(45) Date of Patent: *Apr. 13, 2021

(54) PERFORMANCE-ENHANCED AND TEMPERATURE-RESISTANT PROTEASE VARIANTS

(71) Applicant: Henkel AG & Co. KGaA, Duesseldorf (DE)

(72) Inventors: Hendrik Hellmuth, Darmstadt (DE); Marion Merkel, Cologne (DE); Brian Laufs, Juechen (DE); Susanne Wieland, Dormagen (DE); Timothy O'Connell, Landsberg am Lech (DE); Susanne Tondera, Duesseldorf (DE); Thomas Weber, Dormagen (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/331,850

(22) Filed: Oct. 22, 2016

(65) Prior Publication Data

US 2017/0037343 A1    Feb. 9, 2017

Related U.S. Application Data

(60) Division of application No. 14/261,912, filed on Apr. 25, 2014, now abandoned, which is a continuation of application No. PCT/EP2012/070721, filed on Oct. 19, 2012.

(30) Foreign Application Priority Data

Oct. 28, 2011    (DE) .................... 10 2011 118 021.8

(51) Int. Cl.
| | | |
|---|---|---|
| C11D 3/386 | (2006.01) | |
| C12N 9/54 | (2006.01) | |
| C12N 9/48 | (2006.01) | |

(52) U.S. Cl.
CPC ............... *C11D 3/386* (2013.01); *C12N 9/48* (2013.01); *C12N 9/54* (2013.01); *C12Y 304/21062* (2013.01)

(58) Field of Classification Search
CPC ........................ C11D 3/386; C12Y 304/21062
USPC ........................................... 510/306; 435/212
See application file for complete search history.

(56) References Cited

U.S. PATENT DOCUMENTS

| | | |
|---|---|---|
| 5,340,735 A | 8/1994 | Christianson et al. |
| 5,500,364 A | 3/1996 | Christianson et al. |
| 5,801,039 A | 9/1998 | Maurer et al. |
| 5,985,639 A | 11/1999 | Christianson et al. |
| 6,136,553 A | 10/2000 | Christianson et al. |
| 6,403,331 B1 | 6/2002 | Christianson et al. |
| 7,691,618 B2 | 4/2010 | Wieland et al. |
| 2010/0210502 A1* | 8/2010 | Ghosh .................. C11D 3/2089 510/392 |
| 2011/0237487 A1 | 9/2011 | Souter et al. |
| 2012/0238005 A1 | 9/2012 | Wieland et al. |

FOREIGN PATENT DOCUMENTS

| | | | | |
|---|---|---|---|---|
| EP | 1 921 147 | * | 5/2008 | ............. C12N 15/57 |
| WO | 95/23221 A1 | | 8/1995 | |
| WO | WO-2009030632 A1 | * | 3/2009 | ........... C11D 3/2089 |
| WO | 2009/121725 A1 | | 10/2009 | |

OTHER PUBLICATIONS

Ghosh et al, 2009, WO2009030632. Machine translation.*
PCT International Search Report (PCT/EP2012/070721) dated Nov. 1, 2013.
Gornall et al., "Determination of Serum Proteins by Means of the Biuret Reaction", Journal of Biological Chemistry, vol. 177, pp. 751-766, 1948.
Bender et al., "The Determination of the Concentration of Hydrolytic Enzyme Solutions: a-Chymotrypsin, Trypsin, Papain, Elastase, Subtilisin, and Acetylcholinesterase", Journal of the American Chemical Society, vol. 88:24, pp. 5890-5913, 1966.
Van Raay et al., "The Determination of Proteolytic Activity in Enzyme Concentrates and Enzyme Containing Detergents", Tenside Detergents, vol. 7, No. 3, pp. 125-132, 1970.
Delmar et al., "A Sensitive New Substrate for Chymotrypsin", Analytical Biochemistry, vol. 99, pp. 316-320, 1979.
Kawamura et al., "Construction of a Bacillus subtilis Double Mutant Deficient in Extracellular Alkaline and Neutral Proteases", Journal of Bacteriology, vol. 160, No. 1, pp. 442-444, 1984.
Altschul et al., "Basic Local Alignment Search Tool", Journal of Molecular Biology, vol. 215, pp. 403-410, 1990.

(Continued)

*Primary Examiner* — Sheridan Swope
(74) *Attorney, Agent, or Firm* — Thomas G. Krivulka

(57) ABSTRACT

Proteases that comprise an amino acid sequence that is at least 70% identical to the amino acid sequence indicated in SEQ ID NO. 1 over its entire length and that comprise, in the count in accordance with SEQ ID NO. 1, the amino acid substitution R99D in combination with at least two further amino acid substitutions that are selected from the group consisting of S3T, V4I, and V199I, display very good cleaning performance in particular on blood-containing stains, as well as very good temperature stability.

2 Claims, No Drawings

Specification includes a Sequence Listing.

(56) References Cited

OTHER PUBLICATIONS

Siezen, "Subtilases: Subtilisin-like Serine Proteases", Subtilisin Enzymes: Practical Protein Engineering, pp. 75-93, Plenum Press, New York, 1996.
Altschul et al., "Gapped BLAST and PSI-BLAST: A New Generation of Protein Database Search Programs", Nucleic Acids Research, vol. 25, No. 17, pp. 3389-3402, 1997.
Notredame et al., "T-Coffee: A Novel Method for Fast and Accurate Multiple Sequence Alignment", Journal of Molecular Biology, vol. 302, pp. 205-217, 2000.
Chenna et al., "Multiple Sequence Alignment with the Clustal Series of Programs", Nucleic Acids Research, vol. 31, No. 13, pp. 3497-3500, 2003.

\* cited by examiner

PERFORMANCE-ENHANCED AND TEMPERATURE-RESISTANT PROTEASE VARIANTS

CROSS REFERENCE TO RELATED APPLICATION

This application is a divisional of U.S. application Ser. No. 14/261,912, filed on Apr. 25, 2014, which is a continuation of International Patent Application No. PCT/EP2012/070721, filed Oct. 19, 2012, which claims priority to DE 10 2011 118 021.8, filed Oct. 28, 2011, by which all are hereby incorporated by reference in their entirety.

FIELD OF THE INVENTION

The present invention generally relates to enzyme technology, and more particularly relates to proteases, and to the manufacture thereof, whose amino acid sequence has been modified in particular with regard to use in washing and cleaning agents; to all sufficiently similar proteases having a corresponding modification; and to nucleic acids coding for them. The invention further relates to methods and uses of these proteases and to agents, in particular washing and cleaning agents, containing them.

BACKGROUND OF THE INVENTION

Proteases are among the technically most important of all enzymes. For washing and cleaning agents they are the longest-established enzymes, contained in practically all modern high-performance washing and cleaning agents. They cause the breakdown of protein-containing stains on the material to be cleaned. Among these in turn, proteases of the subtilisin type (subtilases, subtilopeptidases, EC 3.4.21.62), which are categorized among the serine proteases because of the catalytically effective amino acids, are particularly important. They act as nonspecific endopeptidases and hydrolyze any acid amide bonds that are located within peptides or proteins. Their optimum pH is usually in the markedly alkaline range. An overview of this family is offered, for example, by the article "Subtilases: subtilisin-like proteases" by R. Siezen, in "Subtilisin enzymes" pp. 75-95, edited by R. Bott and C. Betzel, New York, 1996. Subtilases are formed naturally by microorganisms; among them, the subtilisins formed and secreted by *Bacillus* species are to be mentioned in particular as the most significant group within the subtilases.

Examples of proteases of the subtilisin type used with preference in washing and cleaning agents are the subtilisins BPN' and Carlsberg, protease PB92, subtilisins 147 and 309, the protease from *Bacillus lentus*, in particular from *Bacillus lentus* DSM 5483, subtilisin DY, and the enzymes (to be classified, however, as subtilases and no longer as subtilisins in the strict sense) thermitase, proteinase K, and the proteases TW3 and TW7, as well as variants of the aforesaid proteases that comprise an amino acid sequence modified as compared with the initial protease. Proteases are modified in controlled or random fashion using methods known from the existing art, and are thereby optimized, for example, for use in washing and cleaning agents. These include point mutagenesis, deletion or insertion mutagenesis, or fusion with other proteins or protein parts. Correspondingly optimized variants are thus known for most proteases known from the existing art.

The international patent applications WO 95/23221 and WO 92/21760 disclose variants of the alkaline protease from *Bacillus lentus* DSM 5483 that are suitable for use in washing or cleaning agents. The international patent application WO 2011/032988 furthermore discloses washing and cleaning agents that likewise contain variants of the alkaline protease from *Bacillus lentus* DSM 5483. The protease variants disclosed in these documents can be modified (in addition to further positions) at positions 3, 4, 99, and 199 in the count of the alkaline protease from *Bacillus lentus* DSM 5483, and can comprise at the aforesaid positions, for example, the amino acids 3T, 4I, 99D, 99E, or 199I. Combinations of these modifications as described hereinafter are, however, not evident from these documents.

It has now been found, surprisingly, that a protease of the type of the alkaline protease from *Bacillus lentus* DSM 5483 or a protease sufficiently similar thereto (based on sequence identity), which comprises several of these modifications in combination, is particularly suitable for use in washing or cleaning agents and is advantageously improved in particular with regard to washing performance and/or stability.

The subject matter of the invention is a protease comprising an amino acid sequence that is at least 70% identical to the amino acid sequence indicated in SEQ ID NO. 1 over its entire length, and comprises, in the count in accordance with SEQ ID NO. 1, the amino acid substitution R99E or R99D in combination with at least two further amino acid substitutions that are selected from the group consisting of S3T, V4I, and V199I.

A further subject of the invention is a method for manufacturing a protease, comprising the introduction of an amino acid substitution R99E or R99D, in combination with at least two further amino acid substitutions that are selected from the group consisting of S3T, V4I, and V199I, in the count in accordance with SEQ ID NO. 1, into an initial protease that is at least 70% identical to the amino acid sequence indicated in SEQ ID NO. 1 over its entire length.

A "protease" for purposes of the present patent application therefore encompasses both the protease as such and a protease manufactured with a method according to the present invention. All statements with regard to the protease therefore refer both to the protease as a substance and to the corresponding method, in particular method for manufacturing the protease.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A protease comprising an amino acid sequence that is at least 70% identical to the amino acid sequence indicated in SEQ ID NO. 1 over its entire length and comprises, in the count in accordance with SEQ ID NO. 1, the amino acid substitution R99E or R99D in combination with at least two further amino acid substitutions that are selected from the group consisting of S3T, V4I, and V199I.

A method for manufacturing a protease, comprising the introduction of an amino acid substitution R99E or R99D, in combination with at least two further amino acid substitutions that are selected from the group consisting of S3T, V4I, and V199I, in the count according to SEQ ID NO. 1, into a starting protease that is at least 70% identical to the amino acid sequence indicated in SEQ ID NO. 1 over its entire length.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Associated with the proteases according to the present invention respectively the manufacturing methods for proteases according to the present invention, as further subjects of the invention, are nucleic acids coding for said proteases, proteases or nucleic acids according to the present invention containing non-human host cells, as well as agents, in particular washing and cleaning agents, washing and cleaning methods, and uses defined by way of proteases according to the present invention, comprising proteases according to the present invention.

A modification according to the present invention of position 99, namely an R99E or R99D modification, in combination with a modification of at least two of positions 3, 4, and 199, namely S3T, V4I, or V199I, in a protease that comprises an amino acid sequence at least 70% identical to the amino acid sequence indicated in SEQ ID NO. 1, preferably brings about improved performance of that modified protease in washing and cleaning agents on at least one protease-sensitive stain. Proteases according to the present invention consequently make possible improved removal of at least one, preferably of several protease-sensitive stains on textiles and/or on hard surfaces, for example dishes. Preferred embodiments of proteases according to the present invention exhibit particularly advantageous cleaning performance on blood-containing stains, for example on the following stains:

blood on cotton: product no. 111 obtainable from Eidgenössische Material-und Prüfanstalt (EMPA) Testmaterialen AG [Swiss federal materials and testing agency test materials], St. Gallen, Switzerland;

milk/carbon black on cotton: (wfk—Cleaning Technology Institute e.V., Krefeld, Germany);

blood-milk/ink on cotton: product no. C-05 obtainable from CFT (Center For Testmaterials) B.V., Vlaardingen, Netherlands.

Preferred embodiments of the present invention consequently make available stain-specific proteases whose cleaning performance is advantageous specifically with regard to one stain or to several stains. The stain focus of preferred embodiments of proteases according to the present invention with regard to blood-containing stains is consequently improved.

Preferred embodiments of proteases according to the present invention already achieve such advantageous cleaning performance effects even at low temperatures between 10° C. and 60° C., between 15° C. and 50° C., and between 20° C. and 40° C. Further preferred embodiments of proteases according to the present invention achieve improved cleaning performance of this kind over a broad temperature range, for example between 15° C. and 90° C., preferably between 20° C. and 60° C.

In addition, preferred embodiments of proteases according to the present invention possess particular stability in washing or cleaning agents, for example with respect to surfactants and/or bleaching agents and/or with respect to temperature influences, in particular with respect to high or low temperatures, for example between 50 and 65° C., in particular 60° C., and/or with respect to acidic or alkaline conditions and/or with respect to changes in pH and/or with respect to denaturing or oxidizing agents and/or with respect to proteolytic breakdown and/or with respect to a change in redox conditions. With particularly preferred embodiments of the invention, protease variants that have improved performance and/or are more temperature-stable are therefore made available. With further very particularly preferred embodiments of the invention, protease variants that have improved performance and are more temperature-stable are made available. These advantageous embodiments of proteases according to the present invention consequently make possible improved washing results on protease-sensitive stains over a broad temperature range.

With regard to the international patent applications WO 95/23221, WO 92/21760, and WO 2011/032988 mentioned initially, the present invention is therefore a particularly advantageous selection of combinations of sequence modifications, the result of which is to obtain a particularly high-performance and/or temperature-stable protease variant for washing or cleaning agents.

"Cleaning performance" is understood in the context of the invention as lightening performance on one or more stains, in particular on laundry or dishes. In the context of the invention, both the washing or cleaning agent that comprises the protease particularly the washing or cleaning bath constituted by said agent, and the protease itself, have a respective cleaning performance. The cleaning performance of the enzyme thus contributes to the cleaning performance of the agent or of the washing or cleaning bath constituted by the agent. The cleaning performance is preferably ascertained as indicated below.

A protease according to the present invention exhibits a proteolytic activity, i.e. it is capable of hydrolyzing peptide bonds of a polypeptide or protein, in particular in a washing or cleaning agent. A protease according to the present invention is therefore an enzyme that catalyzes the hydrolysis of peptide bonds and is thereby capable of cleaving peptides or proteins. A protease according to the present invention is furthermore preferably a mature protease, i.e. the catalytically active molecule having no signal peptide(s) and/or propeptide(s). Unless otherwise indicated, the sequences indicated also refer in each case to mature enzymes.

In a further embodiment of the invention, the protease comprises an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99E in combination with at least two further amino acid substitutions that are selected from the group consisting of S3T, V4I, and V199I.

In a further embodiment of the invention, the protease comprises an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99D in combination with at least two further amino acid substitutions that are selected from the group consisting of S3T, V4I, and V199I.

Particularly preferred proteases according to the present invention are:

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99E in combination with the amino acid substitutions S3T and V4I, in particular a protease in accordance with SEQ ID NO. 1 having the amino acid substitutions S3T, V4I, and R99E.

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99E in combination with the amino acid substitutions S3T and V199I, in particular a protease in accordance with SEQ ID NO. 1 having the amino acid substitutions S3T, R99E, and V199I.

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99E in combination with the amino acid substitutions V4I and V199I, in particular a protease in accordance with SEQ ID NO. 1 having the amino acid substitutions V4I, R99E, and V199I.

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99D in combination with the amino acid substitutions S3T and V4I, in particular a protease in accordance with SEQ ID NO. 1 having the amino acid substitutions S3T, V4I, and R99D.

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99D in combination with the amino acid substitutions S3T and V199I, in particular a protease in accordance with SEQ ID NO. 1 having the amino acid substitutions S3T, R99D, and V199I.

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99D in combination with the amino acid substitutions V4I and V199I, in particular a protease in accordance with SEQ ID NO. 1 having the amino acid substitutions V4I, R99D, and V199I.

Further particularly preferred embodiments of proteases according to the present invention are notable for the fact that they comprise the amino acid substitution R99E or R99D in combination with the three further amino acid substitutions S3T, V4I, and V199I. The following proteases in particular are very particularly preferred in this regard:

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99E in combination with the amino acid substitutions S3T, V4I, and V199I, in particular a protease in accordance with SEQ ID NO. 1 having the amino acid substitutions S3T, V4I, R99E, and V199I. A protease of this kind is indicated in SEQ ID NO. 2.

A protease comprising an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, and 98.8% identical to the amino acid sequence indicated in SEQ ID NO. 1 over its entire length and comprises, in the count in accordance with SEQ ID NO. 1, the amino acid substitution R99D in combination with the amino acid substitutions S3T, V4I, and V199I, in particular a protease in accordance with SEQ ID NO. 1 having the amino acid substitutions S3T, V4I, R99D, and V199I. A protease of this kind is indicated in SEQ ID NO. 3.

Further particularly preferred proteases are proteases as described above that furthermore comprise the amino acid leucine (L) at position 211 in the count in accordance with SEQ ID NO. 1.

The identity of nucleic acid sequences or amino acid sequences is determined by means of a sequence comparison. This sequence comparison is based on the BLAST algorithm that is established in the existing art and usually used (cf. for example Altschul, S. F., Gish, W., Miller, W., Myers, E. W., & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs," Nucleic Acids Res., 25, pp. 3389-3402), and is effected in principle by mutually associating similar successions of nucleotides or amino acids in the nucleic acid sequences or amino acid sequences. A tabular association of the relevant positions is referred to as an "alignment." A further algorithm available in the existing art is the FASTA algorithm. Sequence comparisons (alignments), in particular multiple sequence comparisons, are prepared using computer programs. The Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-

217), or programs based on these programs or algorithms, are often used. In the present patent application, all the sequence comparisons (alignments) were prepared using the computer program Vector NTI® Suite 10.3 (Invitrogen Corporation, 1600 Faraday Avenue, Carlsbad, Calif., USA) with the predefined default parameters, whose AlignX module for the sequence comparisons is based on ClustalW.

A comparison of this kind also allows a statement as to the similarity to one another of the sequences that are being compared. This is usually indicated as a percentage identity, i.e. the proportion of identical nucleotides or amino acid residues at the same positions, or at positions corresponding to one another in an alignment. The more broadly construed term "homology" also, in the context of amino acid sequences, incorporates consideration of the conserved amino acid exchanges, i.e. amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous or identical regions of various nucleic acid sequences or amino acid sequences are therefore defined by way of matches in the sequences. Such regions often have identical functions. They can be small, and can comprise only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity or homology in the present application refer to the full length of the respectively indicated nucleic acid sequence or amino acid sequence.

In a further preferred embodiment of the invention, the protease is characterized in that its cleaning performance corresponds at least to that of a protease that comprises an amino acid sequence that corresponds to the amino acid sequence indicated in SEQ ID NO. 2, and/or at least to that of a protease that comprises an amino acid sequence that corresponds to the amino acid sequence indicated in SEQ ID NO. 3, the cleaning performance being determined in a washing system that contains a washing agent at a dosing ratio of between 4.5 and 7.0 grams per liter of washing bath as well as the protease, the proteases to be compared being used at identical concentration (based on active protein), and the cleaning performance being determined with respect to a blood stain on cotton, in particular with respect to the blood on cotton stain, product no. 111 obtainable from Eidgenössische Material-und Prüfanstalt (EMPA) Testmaterialien AG, St. Gallen, Switzerland, by measuring the whiteness of the washed textiles, the washing procedure being performed for at least 70 minutes at a temperature of 40° C., and the water having a water hardness between 15.5 and 16.5° (German degrees of hardness). The concentration of protease in the washing agent stipulated for this washing system is from 0.001 to 0.1 wt %, preferably 0.01 to 0.06 wt %, based on active protein.

A preferred liquid washing agent for a washing system of this kind has the following composition (all indications in percentage by weight): 0.3 to 0.5% xanthan, 0.2 to 0.4% antifoaming agent, 6 to 7% glycerol, 0.3 to 0.5% ethanol, 4 to 7% FAEOS (fatty alcohol ether sulfate), 24 to 28% nonionic surfactants, 1% boric acid, 1 to 2% sodium citrate (dihydrate), 2 to 4% soda, 14 to 16% coconut fatty acids, 0.5% HEDP (1-hydroxyethane-(1,1-diphosphonic acid)), 0 to 0.4% PVP (polyvinylpyrrolidone), 0 to 0.05% optical brightener, 0 to 0.001% dye, remainder deionized water. The dosing ratio of the liquid washing agent is preferably between 4.5 and 6.0 grams per liter of washing bath, for example 4.7, 4.9, or 5.9 grams per liter of washing bath. Washing preferably occurs in a pH range between pH 8 and pH 10.5, preferably between pH 8 and pH 9.

A preferred powdered washing agent for a washing system of this kind has the following composition (all indications in percentage by weight): 10% linear alkylbenzenesulfonate (sodium salt), 1.5% C12 to C18 fatty alcohol sulfate (sodium salt), 2.0% C12 to C18 fatty alcohol with 7 EO, 20% sodium carbonate, 6.5% sodium hydrogen carbonate, 4.0% amorphous sodium disilicate, 17% sodium carbonate peroxohydrate, 4.0% TAED, 3.0% polyacrylate, 1.0% carboxymethyl cellulose, 1.0% phosphonate, 27% sodium sulfate; remainder: foam inhibitors, optical brighteners, scents. The dosing ratio of the powdered washing agent is preferably between 4.5 and 7.0 grams per liter of washing bath, for example and particularly preferably 4.7 grams per liter of washing bath, or 5.5, 5.9, or 6.7 grams per liter of washing bath. Washing preferably occurs in a pH range between pH 9 and pH 11.

Determination of the cleaning performance at 40° C. is performed in the context of the invention using a solid washing agent as indicated above, the washing operation occurring preferably for 70 minutes.

The whiteness, i.e. the lightening of the stains, is determined as an indication of washing performance, preferably using optical measurement methods, preferably photometrically. An instrument suitable for this is, for example, the Minolta CM508d spectrometer. The instruments used for measurement are usually calibrated beforehand using a white standard, preferably a white standard provided with the unit.

Methods for determining protease activities are familiar to one skilled in the art of enzyme technology, and are applied by him or her on a routine basis. Such methods are disclosed, for example, in Tenside, Vol. 7 (1970), pp. 125-132. Alternatively, the protease activity can be determined quantitatively by way of the release of para-nitroaniline (pNA) chromophore from the suc-L-Ala-L-Ala-L-Pro-L-Phe-p-nitroanilide substrate (AAPF). The protease cleaves the substrate and releases pNA. The release of pNA causes an increase in extinction at 410 nm, the change in which over time is an indication of enzymatic activity (see Del Mar et al., 1979). Measurement is performed at a temperature of 25° C., at pH 8.6, and a wavelength of 410 nm. The measurement time is 5 min, and the measurement interval 20 s to 60 s. The protease activity is usually indicated in protease units (PU). Suitable protease activities, for example, are 2.25, 5 or 10 PU per ml of washing bath. The protease activity is not, however, equal to zero.

The protein concentration can be determined with the aid of known methods, for example the BCA method (bichinchoninic acid; 2,2'-biquinolyl-4,4'-dicarboxylic acid) or the biuret method (A. G. Gornall, C. S. Bardawill and M. M. David, J. Biol. Chem., 177 (1948), pp. 751-766). The active protein concentration can be determined, in this regard, by titrating the active centers using a suitable irreversible inhibitor (for proteases, for example, phenylmethylsulfonyl fluoride (PMSF)), and determining the residual activity (cf. M. Bender et al., J. Am. Chem. Soc. 88, 24 (1966), pp. 5890-5913).

By reaction with an antiserum or a specific antibody, proteins can be combined into groups of immunologically related proteins. The members of such a group are notable for the fact that they comprise the same antigenic determinants that are recognized by an antibody. They are therefore structurally so similar to one another that they are detected by an antiserum or by specific antibodies. A further subject of the invention is therefore constituted by proteases which are characterized in that they comprise at least one and increasingly preferably two, three, or four antigenic determinants matching a protease according to the present invention. Because of their immunological matches, such proteases are structurally so similar to the proteases according to the present invention that a similar function is also be assumed.

In addition to the amino acid modifications explained above, proteases according to the present invention can comprise further amino acid modifications, in particular amino acid substitutions, insertions, or deletions. Such proteases are, for example, further developed by targeted genetic modification, i.e. by way of mutagenesis methods, and optimized for specific purposes or with regard to special properties (for example, with regard to their catalytic activity, stability, etc.). In addition, nucleic acids according to the present invention can be introduced into recombination formulations and thereby used to generate entirely novel proteases or other polypeptides.

The objective is to introduce targeted mutations, such as substitutions, insertions, or deletions, into the known molecules in order, for example, to improve the cleaning performance of enzymes according to the present invention. For this purpose, in particular, the surface charges and/or isoelectric point of the molecules, and thereby their interactions with the substrate, can be modified. For example, the net charge of the enzymes can be modified in order thereby to influence substrate bonding, in particular for use in washing and cleaning agents. Alternatively or additionally, the stability of the protease can be enhanced by way of one or more corresponding mutations, and its cleaning performance thereby improved. Advantageous properties of individual mutations, e.g. individual substitutions, can supplement one another. A protease already optimized with regard to specific properties, for example with regard to its stability in terms of surfactants and/or bleaching agents and/or other components, can therefore be additionally refined in the context of the invention.

The following convention is used to describe substitutions that relate to exactly one amino acid position (amino acid exchanges): Firstly the amino acid that is naturally present is designated in the form of the internationally usual single-letter code; this is followed by the relevant sequence position, and lastly by the inserted amino acid. Multiple exchanges within the same polypeptide chain are separated from one another by slashes. For insertions, additional amino acids are named after the sequence position. For deletions, the missing amino acid is replaced by a symbol, for example an asterisk or a dash. For example, "A95G" describes the substitution of alanine at position 95 with glycine; "A95AG" describes the insertion of glycine after the amino acid alanine at position 95; and "A95*" describes the deletion of alanine at position 95. This nomenclature is known to one skilled in the art of enzyme technology.

A further subject of the invention is therefore a protease which is characterized in that it is obtainable from a protease as described above as an initial molecule by single or multiple conservative amino acid substitution, the protease still comprising, in the count in accordance with SEQ ID NO. 1, the amino acid substitution R99E or R99D in combination with at least two further amino acid substitutions that are selected from the group consisting of S3T, V4I, and V199I, as described above. The term "conservative amino acid substitution" means the exchange (substitution) of one amino acid residue for another amino acid residue, where such exchange does not lead to a change in the polarity or charge at the position of the exchanged amino acid, e.g. the exchange of a nonpolar amino acid residue for another nonpolar amino acid residue. Conservative amino acid substitutions in the context of the invention encompass, for example, G=A=S, I=V=L=M, D=E, N=Q, K=R, Y=F, S=T, G=A=I=V=L=M=Y=F=W=P=S=T.

Alternatively or additionally, the protease is characterized in that it is obtainable from a protease according to the present invention as an initial molecule by fragmentation or by deletion mutagenesis, insertion mutagenesis, or substitution mutagenesis, and comprises an amino acid sequence that matches the initial molecule over a length of at least 50, 60, 70, 80, 90, 100, 110, 120, 130, 140, 150, 160, 170, 180, 190, 200, 210, 220, 230, 240, 250, 260, 265, or 266 continuously connected amino acids, the amino acid substitution R99E or R99D contained in the initial molecule, in combination with at least two further amino acid substitutions that are selected from the group consisting of S3T, V4I, and V199I, still being present, as described above.

It is thus possible, for example, to delete individual amino acids at the termini or in the loops of the enzyme with no loss of or diminution in proteolytic activity as a result. Furthermore, for example, the allergenicity of relevant enzymes can also be decreased by way of such fragmentation or deletion mutagenesis, insertion mutagenesis, or substitution mutagenesis, thus improving its overall usability. Advantageously, the enzymes retain their proteolytic activity even after mutagenesis, i.e. their proteolytic activity corresponds at least to that of the initial enzyme. Substitutions, too, can exhibit advantageous effects. Both individual and multiple continuously connected amino acids can be exchanged for other amino acids.

Alternatively or additionally, the protease is characterized in that it is obtainable from a protease according to the present invention as an initial molecule by way of one or more amino acid substitutions in positions that are associated in an alignment with the positions 36, 42, 47, 56, 61, 69, 87, 96, 101, 102, 104, 114, 118, 120, 130, 139, 141, 142, 154, 157, 188, 193, 205, 211, 224, 229, 236, 237, 242, 243, 255, and 268 of the protease from *Bacillus lentus* in accordance with SEQ ID NO. 1, where the protease still comprises, in the count in accordance with SEQ ID NO. 1, the amino acid substitution R99E or R99D according to the present invention in combination with at least two further amino acid substitutions that are selected from the group consisting of S3T, V4I, and V199I, as described above. The further amino acid positions are defined here by an alignment of the amino acid sequence of a protease according to the present invention with the amino acid sequence of the protease from *Bacillus lentus* as indicated in SEQ ID NO. 1. The association of the positions is furthermore directed toward the mature protein. This association is also to be utilized, in particular, when the amino acid sequence of a protease according to the present invention comprises a greater number of amino acid residues than the protease from *Bacillus lentus* in accordance with SEQ ID NO. 1. Proceeding from the aforesaid positions in the amino acid sequence of the protease from *Bacillus lentus*, the modification positions in a protease according to the present invention are those that are in fact associated with those positions in an alignment.

Advantageous positions for sequence modifications, in particular substitutions, of the protease from *Bacillus lentus* that, transferred to homologous positions of the proteases according to the present invention, are preferably of significance and impart advantageous functional properties to the protease, are accordingly to be associated with the positions 36, 42, 47, 56, 61, 69, 87, 96, 101, 102, 104, 114, 118, 120, 130, 139, 141, 142, 154, 157, 188, 193, 205, 211, 224, 229, 236, 237, 242, 243, 255, and 268 in an alignment with SEQ ID NO. 1 and thus in the count in accordance with SEQ ID NO. 1. The amino acid residues located in the aforesaid positions in the wild type molecule of the protease from *Bacillus lentus* are the following: S36, N42, A47, T56, G61, T69, E87, A96, A101, I102, S104, N114, H118, A120, S130, S139, T141, S142, S154, S157, A188, V193, G205, L211, A224, K229, S236, N237, N242, H243, N255, respectively T268.

Substitutions 61A, 154D, 154E, A188P, or V193M, for example, are particularly advantageous, to the extent the correspondingly homologous positions in a protease according to the present invention are not already naturally occupied by one of these preferred amino acids.

A further confirmation of a correct association of the amino acids to be modified, i.e. in particular their functional correspondence, can be supplied by comparison experiments in which the two positions associated with one another on the basis of an alignment are modified in the same way in both of the proteases being compared with each other, and an observation is made as to whether the enzymatic activity of the two is modified in the same way. For example, if an amino acid exchange at a specific position of the protease from *Bacillus lentus* in accordance with SEQ ID NO. 1 is accompanied by a modification of an enzymatic parameter, for example an elevation of the $K_M$ value, and if a corresponding modification of the enzymatic parameter, for example therefore likewise an elevation of the $K_M$ value, is observed in a protease variant according to the present invention whose amino acid exchange was achieved by way of the same introduced amino acid, this is to be viewed as a confirmation of this correct association.

All the aforementioned facts are also applicable to the method according to the present invention for manufacturing a protease. A method according to the present invention therefore further comprises one or more of the following method steps:
(a) introducing a single or multiple conservative amino acid substitution, where the protease comprises, in the count in accordance with SEQ ID NO. 1, the amino acid substitution R99E or R99D in combination with at least two further amino acid substitutions that are selected from the group consisting of S3T, V4I, and V199I;
(b) modifying the amino acid sequence by fragmentation or by deletion mutagenesis, insertion mutagenesis, or substitution mutagenesis, in such a way that the protease comprises an amino acid sequence that matches the initial molecule over a length of at least 50, 60, 70, 80, 90, 100, 110, 120, 130, 140, 150, 160, 170, 180, 190, 200, 210, 220, 230, 240, 250, 260, 265, or 266 continuously connected amino acids, where the amino acid substitution R99E or R99D contained in the initial molecule, in combination with at least two further amino acid substitutions that are selected from the group consisting of S3T, V4I, and V199I, is still present;
(c) introducing a single or multiple amino acid substitution into one or more of the positions that are associated in an alignment with the positions 36, 42, 47, 56, 61, 69, 87, 96, 101, 102, 104, 114, 118, 120, 130, 139, 141, 142, 154, 157, 188, 193, 205, 211, 224, 229, 236, 237, 242, 243, 255, and 268 of the protease from *Bacillus lentus* in accordance with SEQ ID NO. 1, where the protease comprises, in the count in accordance with SEQ ID NO. 1, the amino acid substitution R99E or R99D in combination with at least two further amino acid substitutions that are selected from the group consisting of S3T, V4I, and V199I.

All the statements also apply to the methods according to the present invention.

In further embodiments of the invention, the protease respectively the protease manufactured with a method according to the present invention is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8% identical to the amino acid sequence indicated in SEQ ID NO. 1 over its entire length. The protease respectively the protease manufactured with a method according to the present invention comprises the amino acid substitution R99E or R99D in combination with at least two further amino acid substitutions that are selected from the group consisting of S3T, V4I, and V199I.

A further subject of the invention is a protease described above that is additionally stabilized, in particular by means of one or more mutations, for example substitutions, or by coupling to a polymer. This is because an increase in stability in the context of storage and/or during use, for example in the washing process, causes the enzymatic activity to last longer and thus causes cleaning performance to be improved. All stabilization possibilities that are described in the existing art and/or are appropriate are suitable in principle. Those stabilization results which are achieved by mutations of the enzyme itself are preferred, since such stabilization requires no further working steps subsequent to recovery of the enzyme. Examples of sequence modifications suitable for this are recited above. Further suitable sequence modifications are known from the existing art. For example, proteases can also be stabilized by exchanging one or more tyrosine residues for other amino acids.

Further possibilities for stabilization are, for example:
modifying the bonding of metal ions, in particular the calcium bonding sites, for example by exchanging one or more of the amino acid(s) participating in calcium bonding for one or more negatively charged amino acids and/or by introducing sequence modifications into at least one of the sequences of the two amino acids arginine and glycine;

protecting against the influence of denaturing agents, such as surfactants, by means of mutations that produce a change in the amino acid sequence on or at the surface of the protein;

exchanging amino acids that are located close to the N terminus for ones that presumably come into contact with the remainder of the molecule via non-covalent interactions, and thus make a contribution to maintaining the globular structure.

Preferred embodiments are those in which the enzyme is stabilized in several ways, since multiple stabilizing mutations have an additive or synergistic effect.

A further subject of the invention is a protease as described above which is characterized in that it comprises at least one chemical modification. A protease having such a modification is referred to as a derivative, i.e. the protease is derivatized.

For purposes of the present Application, "derivatives" are accordingly understood as those proteins whose pure amino acid chain has been chemically modified. Such derivatization operations can be performed, for example, in vivo by the host cell that expresses the protein. Linkages of lowmolecular-weight compounds, such as of lipids or oligosaccharides, are particularly to be emphasized in this context. Derivatizations can also, however, be carried out in vitro, e.g. by chemical conversion of a side chain of an amino acid or by covalent bonding of a different compound onto the protein. Linkage of amines to carboxyl groups of an enzyme in order to modify the isoelectric point is, for example, possible. One such other compound can also be a further protein that is bound, for example, via bifunctional chemical compounds to a protein according to the present invention. "Derivatization" is likewise to be understood as covalent bonding to a macromolecular carrier, or also as a non-covalent inclusion into suitable macromolecular cage structures. Derivatizations can, for example, influence the substrate specificity or strength of bonding to the substrate, or can bring about a temporary blockage of enzymatic activity if the linked-on substance is an inhibitor. This can be useful, for example, for the period of storage. Modifications of this kind can furthermore influence stability or enzymatic activity. They can moreover also serve to decrease the allergenicity and/or immunogenicity of the protein and thereby, for example, increase its skin compatibility. For example, linkages to macromolecular compounds, for example polyethylene glycol, can improve the protein with regard to stability and/or skin compatibility.

"Derivatives" of a protein according to the present invention can also be understood in the broadest sense as preparations of said proteins. Depending on recovery, processing, or preparation, a protein can be brought into association with a variety of other substances, for example from the culture of the producing microorganisms. A protein can also have had other substances deliberately added to it, for example in order to enhance its shelf stability. All preparations of a protein according to the present invention are therefore also in accordance with the present invention. This is also irrespective of whether or not it actually displays this enzymatic activity in a specific preparation. This is because it may be desirable for it to possess little or no activity during storage, and to perform its enzymatic function only at the time of use. This can be controlled, for example, by way of corresponding accompanying substances. The preparation of proteases together with protease inhibitors is a particular possibility in this regard.

With respect to all the proteases or protease variants and/or derivatives described above, those whose activity corresponds at least to that of the protease in accordance with SEQ ID NO. 2 and/or SEQ ID NO. 3, and/or whose cleaning performance corresponds at least to that of the protease in accordance with SEQ ID NO. 2 and/or SEQ ID NO. 3, are particularly preferred in the context of the present invention, the cleaning performance being determined in a washing system as described above.

A further subject of the present invention is a nucleic acid that codes for a protease according to the present invention, as well as a vector containing such a nucleic acid, in particular a cloning vector or an expression vector.

These can be DNA molecules or RNA molecules. They can exist as an individual strand, as an individual strand complementary to said individual strand, or as a double strand. With DNA molecules in particular, the sequences of both complementary strands in all three possible reading frames are to be considered in each case. Also to be considered is the fact that different codons, i.e. base triplets, can code for the same amino acids, so that a specific amino acid sequence can be coded by multiple different nucleic acids. As a result of this degeneracy of the genetic code, all nucleic acid sequences that can encode one of the above-described proteases are included in this subject of the invention. The skilled artisan is capable of unequivocally determining these nucleic acid sequences, since despite the degeneracy of the genetic code, defined amino acids are to be associated with individual codons. The skilled artisan can therefore, proceeding from an amino acid sequence, readily ascertain nucleic acids coding for that amino acid sequence. In addition, in the context of nucleic acids according to the present invention one or more codons can be replaced by synonymous codons. This aspect refers in particular to heterologous expression of the enzymes according to the present invention. For example, every organism, e.g. a host cell of a production strain, possesses a specific codon usage. "Codon usage" is understood as the translation of the genetic code into amino acids by the respective organism. Bottlenecks in protein biosynthesis can occur if the codons located on the nucleic acid are confronted, in the organism, with a comparatively small number of loaded tRNA molecules. Although it codes for the same amino acid, the result is that a codon becomes translated in the organism less efficiently than a synonymous codon that codes for the same amino acid. Because of the presence of a larger number of tRNA molecules for the synonymous codon, the latter can be translated more efficiently in the organism.

By way of methods commonly known today such as, for example, chemical synthesis or the polymerase chain reaction (PCR) in combination with standard methods of molecular biology and/or protein chemistry, a skilled artisan has the ability to manufacture, on the basis of known DNA sequences and/or amino acid sequences, the corresponding nucleic acids all the way to complete genes. Such methods are known, for example, from Sambrook, J., Fritsch, E. F., and Maniatis, T, 2001, Molecular cloning: a laboratory manual, 3rd edition, Cold Spring Laboratory Press.

"Vectors" are understood for purposes of the present invention as elements, made up of nucleic acids, that contain a nucleic acid according to the present invention as a characterizing nucleic acid region. They enable said nucleic acid to be established as a stable genetic element in a species or a cell line over multiple generations or cell divisions. In particular when used in bacteria, vectors are special plasmids, i.e. circular genetic elements. In the context of the present invention, a nucleic acid according to the present invention is cloned into a vector. Included among the vectors are, for example, those whose origins are bacterial plasmids, viruses, or bacteriophages, or predominantly synthetic vectors or plasmids having elements of widely differing origins. Using the further genetic elements present in each case, vectors are capable of establishing themselves as stable units in the relevant host cells over multiple generations. They can be present extrachromosomally as separate units, or can be integrated into a chromosome or into chromosomal DNA.

Expression vectors comprise nucleic acid sequences which are capable of replicating in the host cells, preferably microorganisms, particularly preferably bacteria, that contain them, and expressing therein a contained nucleic acid. Expression is influenced in particular by the promoter or promoters that regulate transcription. Expression can occur in principle by means of the natural promoter originally located in front of the nucleic acid to be expressed, but also by means of a host-cell promoter furnished on the expression vector or also by means of a modified, or entirely different, promoter of another organism or of another host cell. In the present case at least one promoter for expression of a nucleic acid according to the present invention is made available and used for expression thereof. Expression vectors can furthermore be regulatable, for example by way of a change in culture conditions or when the host cells containing them reach a specific cell density, or by the addition of specific substances, in particular activators of gene expression. One example of such a substance is the galactose derivative isopropyl-β-D-thiogalactopyranoside (IPTG), which is used as an activator of the bacterial lactose operon (lac operon). In contrast to expression vectors, in cloning vectors the contained nucleic acid is not expressed.

A further subject of the invention is a non-human host cell that contains a nucleic acid according to the present invention or a vector according to the present invention, or that contains a protease according to the present invention, in particular one that secretes the protease into the medium surrounding the host cell. A nucleic acid according to the present invention or a vector according to the present invention is preferably transformed into a microorganism, which then represents a host cell according to the present invention. Alternatively, individual components, i.e. nucleic acid parts or fragments of a nucleic acid according to the present invention, can be also be introduced into a host cell in such a way that the host cell which then results contains a nucleic acid according to the present invention or a vector according to the present invention. This procedure is suitable in particular when the host cell already contains one or more constituents of a nucleic acid according to the present invention or a vector according to the present invention, and the further constituents are then correspondingly supplemented. Methods for the transformation of cells are established in the existing art and are sufficiently known to the skilled artisan. All cells are in principle suitable as host cells, i.e. prokaryotic or eukaryotic cells. Those host cells that can be manipulated in genetically advantageous fashion, e.g. as regards transformation using the nucleic acid or vector and stable establishment thereof, are preferred, for example single-celled fungi or bacteria. In addition, preferred host cells are notable for being readily manipulated in microbiological and biotechnological terms. This refers, for example, to easy culturability, high growth rates, low demands in terms of fermentation media, and good production and secretion rates for foreign proteins. Preferred host cells according to the present invention secrete the (transgenically) expressed protein into the medium surrounding the host cells. The proteases can furthermore be modified, after their manufacture, by the cells producing them, for example by the addition of sugar molecules, formylation, amination, etc. Post-translation modifications of this kind can functionally influence the protease.

Further preferred embodiments are represented by those host cells whose activity can be regulated on the basis of genetic regulation elements that are made available, for example, on the vector, but can also be present a priori in those cells. They can be stimulated to expression, for example, by controlled addition of chemical compounds that serve as activators, by modifying the culture conditions, or when a specific cell density is reached. This makes possible economical production of the proteins according to the present invention. One example of such a compound is IPTG, as described earlier.

Preferred host cells are prokaryotic or bacterial cells. Bacteria are notable for short generation times and few demands in terms of culturing conditions. As a result, economical culturing methods or manufacturing methods can be established. In addition, the skilled artisan has a great wealth of experience with bacteria in fermentation technology. Gram-negative or Gram-positive bacteria may be suitable for a specific production instance, for a wide variety of reasons to be ascertained experimentally in the individual case, such as nutrient sources, product formation rate, time requirement, etc.

In Gram-negative bacteria such as, for example, *Escherichia coli*, a plurality of proteins are secreted into the periplasmic space, i.e. into the compartment between the two membranes enclosing the cell. This can be advantageous for specific applications. Gram-negative bacteria can furthermore also be configured so that they discharge the expressed proteins not only into the periplasmic space but into the medium surrounding the bacterium. Gram-positive bacteria, on the other hand, such as e.g. bacilli or *actinomycetes*, or other representatives of the actinomycetals, possess no external membrane, so that secreted proteins are delivered immediately into the medium, as a rule the nutrient medium, surrounding the bacteria, from which medium the expressed proteins can be purified. They can be isolated directly from the medium, or further processed. In addition, Gram-positive bacteria are related or identical to most originating organisms for technically important enzymes, and usually themselves form comparable enzymes, so that they possess similar codon usage and their protein synthesis apparatus is of course correspondingly directed.

Host cells according to the present invention can be modified in terms of their requirements for culture conditions, can comprise other or additional selection markers, or can also express other or additional proteins. They can, in particular, be those host cells that transgenically express multiple proteins or enzymes.

The present invention is applicable in principle to all microorganisms, in particular to all fermentable microorganisms, particularly preferably to those of the genus *Bacillus*, and its result is that proteins according to the present invention can be manufactured by the use of such microorganisms. Such microorganisms then represent host cells for purposes of the invention.

In a further embodiment of the invention, the host cell is characterized in that it is a bacterium, preferably one that is selected from the group of the genera *Escherichia, Klebsiella, Bacillus, Staphylococcus, Corynebacterium, Arthrobacter, Streptomyces, Stenotrophomonas*, and *Pseudomonas*, more preferably one that is selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor*, and *Stenotrophomonas maltophilia*.

The host cell can, however, also be a eukaryotic cell, which is characterized in that it possesses a cell nucleus. A further subject of the invention is therefore represented by a host cell which is characterized in that it possesses a cell nucleus. In contrast to prokaryotic cells, eukaryotic cells are capable of post-translationally modifying the protein that is formed. Examples thereof are fungi such as *Actinomycetes*, or yeasts such as *Saccharomyces* or *Kluyveromyces*. This may be particularly advantageous, for example, when the proteins are intended to experience, in connection with their synthesis, specific modifications made possible by such systems. Among the modifications that eukaryotic systems carry out in particular in conjunction with protein synthesis are, for example, the bonding of low-molecular-weight compounds such as membrane anchors or oligosaccharides. Oligosaccharide modifications of this kind can be desirable, for example, in order to decrease the allergenicity of an expressed protein. Co-expression with the enzymes naturally formed by such cells, for example cellulases or lipases, can also be advantageous. Thermophilic fungal expression systems, for example, can furthermore be particularly suitable for the expression of temperature-resistant proteins or variants.

The host cells according to the present invention are cultured and fermented in a usual manner, for example in discontinuous or continuous systems. In the former case a suitable nutrient medium is inoculated with the host cells, and the product is harvested from the medium after a period of time to be ascertained experimentally. Continuous fermentations are notable for the achievement of a flow equilibrium in which, over a comparatively long period of time, cells die off in part but are also in part renewed, and the protein formed can simultaneously be removed from the medium.

Host cells according to the present invention are preferably used to manufacture proteases according to the present invention. A further subject of the invention is therefore a method for manufacturing a protease, comprising
a) culturing a host cell according to the present invention
b) isolating the protease from the culture medium or from the host cell.

This subject of the invention preferably comprises fermentation methods. Fermentation methods are known from the existing art and represent the actual industrial-scale production step, generally followed by a suitable method for purifying the product that was manufactured, for example the protease according to the present invention. All fermentation methods that are based on a corresponding method for manufacturing a protease according to the present invention correspondingly represent embodiments of this subject of the invention.

Fermentation methods which are characterized in that fermentation is carried out by way of an inflow strategy are particularly appropriate. In this context the constituents of the medium that are consumed during continuous culturing are fed in. Considerable increases both in cell density and in cell mass or dry mass, and/or principally in the activity of the protease of interest, can thereby be achieved. In addition, the fermentation operation can also be configured so that undesired metabolic products are filtered out, or are neutralized by the addition of a buffer or respectively suitable counterions.

The protease that has been manufactured can be harvested from the fermentation medium. A fermentation method of this kind is preferred over isolation of the protease from the host cell, i.e. product preparation from the cell mass (dry mass), but requires that suitable host cells, or one or more suitable secretion markers respectively mechanisms and/or transport systems, be made available so that the host cells secrete the protease into the fermentation medium. Alternatively, without secretion, isolation of the protease from the host cell can occur, i.e. purification thereof from the cell mass, for example by precipitation using ammonium sulfate or ethanol, or by chromatographic purification.

All the above facts can be combined into methods for manufacturing proteases according to the present invention.

A further subject of the invention is an agent which is characterized in that it contains a protease according to the present invention as described above. The agent is preferably a washing or cleaning agent. Because proteases according to the present invention exhibit advantageous cleaning performance effects in particular on blood-containing stains, the agents are suitable and advantageous in particular for removing such stains.

Included in this subject of the invention are all conceivable types of washing or cleaning agents, both concentrates and agents to be used undiluted, for use on a commercial scale, in washing machines, or for hand laundering or cleaning. Included thereamong are, for example, washing agents for textiles, carpets, or natural fibers, for which the term "washing agent" is used. Also included thereamong are, for example, dishwashing agents for automatic dishwashers, or manual dishwashing agents, or cleaners for hard surfaces such as metal, glass, porcelain, ceramic, tiles, stone, painted surfaces, plastics, wood, or leather, for which the term "cleaning agent" is used, i.e. in addition to manual and automatic dishwashing agents, for example also scouring agents, glass cleaners, toilet cleaners, etc. Further included among the washing and cleaning agents in the context of the invention are washing adjuvants that are dispensed into the actual washing agent in the context of manual or automatic textile laundering in order achieve a further effect. Also included among washing and cleaning agents in the context of the invention are textile pre- and post-treatment agents, i.e. those agents with which the laundered item is brought into contact before actual laundering, for example in order to loosen stubborn stains, as well as those agents that, in a step following actual textile laundering, impart to the washed item further desirable properties such as a pleasant feel, absence of creases, or low static charge. The fabric softeners, among others, are classified among the latter agents.

The washing or cleaning agents according to the present invention, which can be present as in particular powdered solids, in recompressed particle form, as homogeneous solutions or suspensions, can contain besides a protease according to the present invention all known ingredients usual in such agents, at least one further ingredient preferably being present in the agent. The agents according to the present invention can contain, in particular, surfactants, builders (detergency builders), peroxygen compounds, or bleach activators. They can further contain water-miscible organic solvents, further enzymes, sequestering agents, electrolytes, pH regulators, and/or further adjuvants such as optical brighteners, anti-gray agents, foam regulators, as well as dyes and scents, as well as combinations thereof.

A combination of a protease according to the present invention with one or more further ingredient(s) of the agent is particularly advantageous, since in preferred configurations according to the present invention such an agent exhibits improved cleaning performance thanks to synergies that result. Such a synergy can be achieved in particular by combining a protease according to the present invention with a surfactant and/or a builder (detergency builder) and/or a peroxygen compound and/or a bleach activator.

Advantageous ingredients of agents according to the present invention are disclosed in the international patent application WO 2009/121725, beginning therein on page 5, next-to-last paragraph and ending on page 13 after the second paragraph. Reference is expressly made to this disclosure, and the disclosure therein is incorporated into the present patent application.

An agent according to the present invention contains the protease advantageously in a quantity from 2 µg to 20 mg, preferably from 5 µg to 17.5 mg, particularly preferably from 20 µg to 15 mg, and very particularly preferably from 50 µg to 10 mg per g of the agent. In addition, the protease contained in the agent, and/or further ingredients of the agent, can be encased with a substance that is impermeable to the enzyme at room temperature or in the absence of water, which substance becomes permeable to the enzyme under utilization conditions of the agent. Such an embodiment of the invention is thus characterized in that the protease is encased with a substance that is impermeable to the protease at room temperature or in the absence of water. In addition, the washing or cleaning agent itself can also be packaged in a container, preferably an air-permeable container, from which it is released shortly before use or during the washing operation.

In further embodiments of the invention, the agent is characterized in that it is
(a) present in solid form, in particular as a pourable powder having a bulk weight from 300 g/l to 1200 g/l, in particular 500 g/l to 900 g/l, or
(b) present in pasty or in liquid form, and/or
(c) present as a one-component system, or
(d) subdivided into multiple components.

These embodiments of the present invention encompass all solid, powdered, liquid, gelled, or pasty administration forms of agents according to the present invention, which optionally can also be made up of multiple phases and can be present in compressed or uncompressed form. The agent can be present as a pourable powder, in particular having a bulk weight from 300 g/l to 1200 g/l, in particular 500 g/l to 900 g/l, or 600 g/l to 850 g/l. Further included among the solid administration forms of the agent are extrudates, granulates, tablets, or pouches. Alternatively, the agent can also be liquid, gelled, or pasty, for example in the form of a nonaqueous liquid washing agent or a nonaqueous paste or in the form of an aqueous liquid washing agent or a hydrous paste. The agent can furthermore be present as a one-component system. Such agents are made up of one phase. Alternatively, an agent can also be made up of multiple phases. An agent of this kind is thus subdivided into multiple components.

Washing or cleaning agents according to the present invention can contain exclusively a protease. Alternatively, they can also contain further hydrolytic enzymes or other enzymes, in a concentration useful for the effectiveness of the agent. A further embodiment of the invention is thus represented by agents that moreover comprise one or more further enzymes. All enzymes that can display catalytic activity in the agent according to the present invention are preferably usable as further enzymes, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase, or a lipase, as well as mixtures thereof. Further enzymes are contained in the agent advantageously in a quantity in each case from $1 \times 10^{-8}$ to 5 weight percent, based on active protein. Increasingly preferably, each further enzyme is contained in agents according to the present invention in a quantity from $1 \times 10^{-7}$ to 3 wt %, from 0.00001 to 1 wt %, from 0.00005 to 0.5 wt %, from 0.0001 to 0.1 wt %, and particularly preferably from 0.0001 to 0.05 wt %, based on active protein. Particularly preferably, the enzymes exhibit synergistic cleaning performance effects with respect to specific stains or spots, i.e. the enzymes contained in the agent composition mutually assist one another in their cleaning performance. Very particularly preferably, a synergism of this kind exists between the protease contained according to the present invention and a further enzyme of an agent according to the present invention, thereamong in particular between the aforesaid protease and the amylase and/or a lipase and/or a mannanase and/or a cellulase and/or a pectinases. Synergistic effects can occur not only between different enzymes, but also between one or more enzymes and further ingredients of the agent according to the present invention.

A further subject of the invention is a method for cleaning textiles or hard surfaces which is characterized in that in at least one method step an agent according to the present invention is utilized; or that in at least one method step a protease according to the present invention becomes catalytically active, in particular in such a way that the protease is used in a quantity from 40 µg to 4 g, preferably from 50 µg to 3 g, particularly preferably from 100 µg to 2 g, and very particularly preferably from 200 µg to 1 g, per utilization.

Included thereamong are both manual and automatic methods, automatic methods being preferred. Methods for cleaning textiles are notable in general for the fact that, in multiple method steps, various substances having cleaning activity are applied onto the material to be cleaned and are washed out after the contact time, or that the material to be cleaned is treated in another fashion with a washing agent or a solution or dilution of said agent. The same applies correspondingly to methods for cleaning all materials other than textiles, in particular hard surfaces. All conceivable washing or cleaning methods can be supplemented, in at least one of the method steps, by the utilization of a washing or cleaning agent according to the present invention or of a protease according to the present invention, and then represent embodiments of the present invention. All facts, subject matters, and embodiments that are described for the proteases according to the present invention or agents containing them are also applicable to this subject of the invention. Reference is therefore expressly made at this juncture to the disclosure at the corresponding juncture, with the instruction that this disclosure is also valid for the present methods according to the present invention.

Because proteases according to the present invention already naturally possess a hydrolytic activity and display it even in media that otherwise possess no cleaning power, for example in pure buffer, an individual and/or the only step of such a method can consist in bringing a protease according to the present invention, if desired as a sole component having cleaning activity, into contact with the stain, preferably in a buffer solution or in water. This represents a further embodiment of this subject of the invention.

Alternative embodiments of this subject of the invention are also represented by methods for treating textile raw materials or for textile care, in which a protease according to the present invention becomes active in at least one method step. Preferred thereamong are methods for textile raw materials, fibers, or textiles having natural constituents, and very particularly for those having wool or silk.

A further subject of the invention is the use of an agent according to the present invention for the cleaning of textiles or hard surfaces, or of a protease according to the present invention for the cleaning of textiles or hard surfaces, in particular in such a way that the protease is used in a quantity from 40 µg to 4 g, preferably from 50 µg to 3 g, particularly preferably from 100 µg to 2 g, and very particularly preferably from 200 µg to 1 g.

All facts, subject matters, and embodiments that are described for the proteases according to the present invention and agents containing them are also applicable to this subject of the invention. Reference is therefore expressly made at this juncture to the disclosure at the corresponding juncture, with the instruction that this disclosure is also valid for the present use according to the present invention.

EXAMPLES

All the molecular-biological working steps follow standard methods such as those indicated, for example, in the manual of Fritsch, Sambrook, and Maniatis, "Molecular cloning: a laboratory manual," Cold Spring Harbor Laboratory Press, New York, 1989, or comparable relevant works. Enzymes and kits were used in accordance with the respective manufacturer's instructions.

Example 1

Proceeding from a protease that comprised an amino acid sequence in accordance with SEQ ID NO. 1, a protease variant according to the present invention was manufactured by site-directed mutagenesis in the nucleic acid coding for the protease, using the PHUSION Site-Directed Mutagenesis Kit (Finnzyme, F541). In this, the codons for the amino acid positions indicated were modified so that, with reference to the amino acid sequence, an exchange of the amino acids occurred as indicated. Expression of the protease variant occurred in a manner usual in the art, by transforming Bacillus subtilis DB 104 (Kawamura and Doi (1984), J. Bacteriol., Vol. 160 (1), pp. 442-444) with a corresponding expression vector and subsequent culturing of the transformands expressing the protease variant.

Protease variant 1: Protease having an amino acid sequence in accordance with SEQ ID NO. 1 having the amino acid substitutions S3T, V4I, R99E, V199I in the count in accordance with SEQ ID NO. 1 (SEQ ID NO. 2);

Protease variant 2: Protease having an amino acid sequence in accordance with SEQ ID NO. 1 having the amino acid substitutions S3T, V4I, R99D, V199I in the count in accordance with SEQ ID NO. 1 (SEQ ID NO. 3).

Example 2

Ascertaining the Cleaning Performance of Proteases According to the Present Invention when Used in a Commercially Usual Liquid Washing Agent Standardized stained textiles were used for this Example. The following stains were used:
A. Blood on cotton: product no. 111 obtainable from Eidgenössische Material-und Prüfanstalt (EMPA) Testmaterialen AG, St. Gallen, Switzerland,
B. Milk/carbon black on cotton (wfk—Cleaning Technology Institute e.V., Krefeld, Germany),
C. Blood-milk/ink on cotton: product no. C-05 obtainable from CFT (Center For Testmaterials) B.V., Vlaardingen, Netherlands.

Using this test material, a variety of washing-agent formulations were investigated in terms of their cleaning performance. For this, the batches were washed for 70 minutes at a temperature of 20° C. or 40° C. The dosing ratio was 4.7 g of washing agent per liter of washing bath. Washing was performed with tap water having a hardness of 16 degrees of German hardness.

A baseline washing-agent formulation of the following composition was used as a control washing agent (all indications in percent by weight): 0.3 to 0.5% xanthan, 0.2 to 0.4% antifoaming agent, 6 to 7% glycerol, 0.3 to 0.5% ethanol, 4 to 7% FAEOS (fatty alcohol ether sulfate), 24 to 28% nonionic surfactants, 1% boric acid, 1 to 2% sodium citrate (dihydrate), 2 to 4% soda, 14 to 16% coconut fatty acid, 0.5% HEDP (1-hydroxyethane-(1,1-diphosphonic acid)), 0 to 0.4% PVP (polyvinylpyrrolidone), 0 to 0.05% optical brightener, 0 to 0.001% dye, remainder deionized water.

The baseline washing-agent formulation had the following proteases added to it on an identical active-protein basis (0.03 wt % active substance), for the various series of experiments. Protease variant 1 (batch 1) from Example 1 was used as a protease according to the present invention. The reference used was a protease that is disclosed in FIG. 2 such as SEQ ID NO. 3 of the international patent application WO 03/057713 (batch 2). This reference protease exhibits very good cleaning performance in liquid washing and cleaning agents.

After washing, the whiteness of the washed textiles was measured. The measurement was carried out on a Minolta CM508d spectrometer (D65 illumination, 10°). The instrument had previously been calibrated using a white standard provided with it. The results obtained are the difference between the remission units obtained for the protease according to the present invention and the remission units obtained for the reference protease (ΔREM=batch 1 remission units–batch 2 remission units). Positive values consequently indicate an improved whiteness for the protease according to the present invention as compared with the reference protease. The results are summarized in Table 1 below.

TABLE 1

Washing results with a liquid washing agent at 20° C. and 40° C.

| Temperature | Stain | ΔREM |
| --- | --- | --- |
| 20° C. | A | 3.7 |
|  | B | 5.9 |
| 40° C. | A | 6.2 |
|  | C | 3.3 |

It is evident that the protease according to the present invention exhibits improved cleaning performance, in particular on blood-containing stains.

Example 3

Ascertaining the Temperature Stability of Proteases According to the Present Invention The proteases indicated below were incubated at a concentration of 10 to 20 µg/ml in 0.1M glycine/NaOH buffer at 60° C. and pH 10.0. At regular intervals over a period of 60 minutes, samples were taken, held on ice, and measured using an activity test by determining residual proteolytic activity via the release of para-nitroaniline (pNA) chromophore from the substrate. The substrate is a suc-L-Ala-L-Ala-L-Pro-L-Phe-p-nitroanilide substrate (suc-AAPF-pNA). The protease cleaves the substrate and releases pNA. The release of pNA causes an increase in extinction at 410 nm, the time course of which is an indication of enzymatic activity (see Del Mar et al., 1979). The half life was calculated based on the residual activity values that were determined. The following half lives (t ½) were obtained:

Measured Half Lives

| Protease used | t ½ (pH 10.0; 60° C.), minutes |
|---|---|
| Protease according to FIG. 2, SEQ ID NO. 3 of WO 03/057713 | 16 |
| Variant of alkaline protease from *Bacillus lentus* DSM 5483 according to WO 92/21760 (modifications at positions 3, 4, and 199) | 94 |
| Protease variant 1 according to the present invention (see Example 1) | 127 |

It is apparent that a protease according to the present invention exhibits appreciably improved temperature stability.

Proteases according to the present invention consequently exhibit improved cleaning performance and are advantageously temperature-stable.

Example 4

Ascertaining the Cleaning Performance of Proteases According to the Present Invention when Used in a Commercially Usual Liquid Washing Agent at a Washing Temperature of 60° C.

Standardized stained textiles were used for this Example. The following stains were used:
a) Stains from Eidgenössische Material-und Prüfanstalt (EMPA) Testmaterialen AG, St. Gallen, Switzerland: EMPA 117 (blood/milk/ink on polyester/cotton), EMPA 112 (cocoa on cotton)
b) Stains from wfk—Cleaning Technology Institute e.V., Krefeld, Germany: 10 EG (egg yolk on cotton), 10N (whole egg/pigment on cotton)
c) Stains from CFT (Center For Testmaterials) B.V., Vlaardingen, Netherlands: CS-01 (blood on cotton), C-05 (blood/milk/ink on cotton), CS-44 (chocolate drink on cotton), CS-37 (whole egg with pigment on cotton), C-10 (pigment/oil/milk on cotton), CS-06 (salad dressing with natural black on cotton), CS-08 (grass on cotton).

Using this test material, a variety of washing agent formulations were investigated in terms of their washing performance. The experiments were carried out as described in Example 2, except that washing occurred at a higher temperature, specifically 60° C. The protease variant 1 (hereinafter batch 1) from Example 1 was used as a protease according to the present invention. The following proteases, which already exhibit very good cleaning performance in liquid washing and cleaning agents, served as references:
Batch 2: variant F49 of the alkaline protease from *Bacillus lentus* DSM 5483 in accordance with WO 95/23221;
Batch 3: variant of the alkaline protease from *Bacillus lentus* DSM 5483 in accordance with WO 92/21760 (modifications at positions 3, 4, and 199);
Batch 4: protease having an amino acid sequence in accordance with SEQ ID NO. 1 having the amino acid substitution R99E in the count in accordance with SEQ ID NO. 1.

Batch 4 served as a standard. The values indicated in Table 3 below represent the sum of the cleaning performance values on all stains as a difference from the standard in accordance with batch 4. Negative values therefore signify poorer cleaning performance as compared with the standard over all stains; positive values signify improved cleaning performance as compared with the standard over all stains.

TABLE 3

| | Batch | | | |
|---|---|---|---|---|
| | 1 | 2 | 3 | 4 |
| Cleaning performance | +10.2 | −20.9 | −24.0 | 0 |

It is apparent that a protease according to the present invention exhibits appreciably improved cleaning performance at 60° C. as well.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A washing or cleaning agent comprising a polypeptide that is at least 98% identical to the amino acid sequence indicated in SEQ ID NO. 1, wherein the polypeptide has protease activity, and comprises in position 99 in the numbering according to SEQ ID NO. 1 the amino acid glutamic acid (E) or aspartic acid (D) and S3T, V4I, and V199I, and comprises, by weight, 0.3 to 0.5% xanthan, 4 to 7% fatty alcohol ether sulfate, 24 to 28% nonionic surfactants and 0.5% 1-hydroxyethane-(1,1-diphosphonic acid).

2. A method for manufacturing the protease of claim 1, comprising introduction of the amino acid substitution R99E or R99D in combination with the amino acid substitutions S3T, V4I, and V199I in the count according to SEQ ID NO. 1.

* * * * *

SEQUENCE LISTING

```
<160> NUMBER OF SEQ ID NOS: 3

<210> SEQ ID NO 1
<211> LENGTH: 269
<212> TYPE: PRT
<213> ORGANISM: Bacillus lentus

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

```
His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 269
<212> TYPE: PRT
<213> ORGANISM: Bacillus lentus

<400> SEQUENCE: 2

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 3
<211> LENGTH: 269
<212> TYPE: PRT
<213> ORGANISM: Bacillus lentus

<400> SEQUENCE: 3

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Asp Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```